United States Patent [19]

Bowers

[11] Patent Number: 5,207,230
[45] Date of Patent: May 4, 1993

[54] SPIRAL SENSOR

[76] Inventor: David L. Bowers, 9385 La Suvida Dr., La Mesa, Calif. 92041

[21] Appl. No.: 831,983

[22] Filed: Feb. 6, 1992

[51] Int. Cl.$^5$ .................................................. A61B 5/103
[52] U.S. Cl. ........................................ 128/780; 128/721
[58] Field of Search .............. 128/721, 722, 723, 782, 128/662.06, 780, 781, 24 R, 2 P, 30.2, 32, 64, 67; 338/2, 6; 33/512; 73/862.64, 862.65, 862,66, 862.67

[56] References Cited

U.S. PATENT DOCUMENTS

| | | | |
|---|---|---|---|
| 4,381,788 | 5/1983 | Douglas | 128/782 X |
| 4,600,017 | 7/1986 | Schroeppel | 128/419 P |
| 4,690,143 | 9/1987 | Schroeppel | 128/419 P |
| 4,807,640 | 2/1989 | Watson et al. | 128/721 |
| 4,815,473 | 3/1989 | Watson et al. | 128/721 |
| 4,817,625 | 4/1989 | Miles | 128/721 |
| 5,070,882 | 12/1991 | Bui et al. | 128/662.06 |

Primary Examiner—Lee S. Cohen
Assistant Examiner—Samuel Gilbert
Attorney, Agent, or Firm—Woodcock, Washburn, Kurtz, Mackiewicz & Norris

[57] ABSTRACT

A sensor has a transducer film attached substantially along a spiral cord. The spiral cord provides flexibility in attaching the sensor to a body portion, and provides that multiple, individual sections along the length thereof come into contact with the patient. The transducer film preferably comprises a piezo film with a metallization surface on each side thereof. A wire conductor is attached along the length of the outer metallization surface to maintain conductive integrity under expected stress levels and situations. In another embodiment, plural layer sensors are formed, having two or more transducer films placed one on top of the other along the length of the sensor, or selected portions of the sensor length.

22 Claims, 7 Drawing Sheets

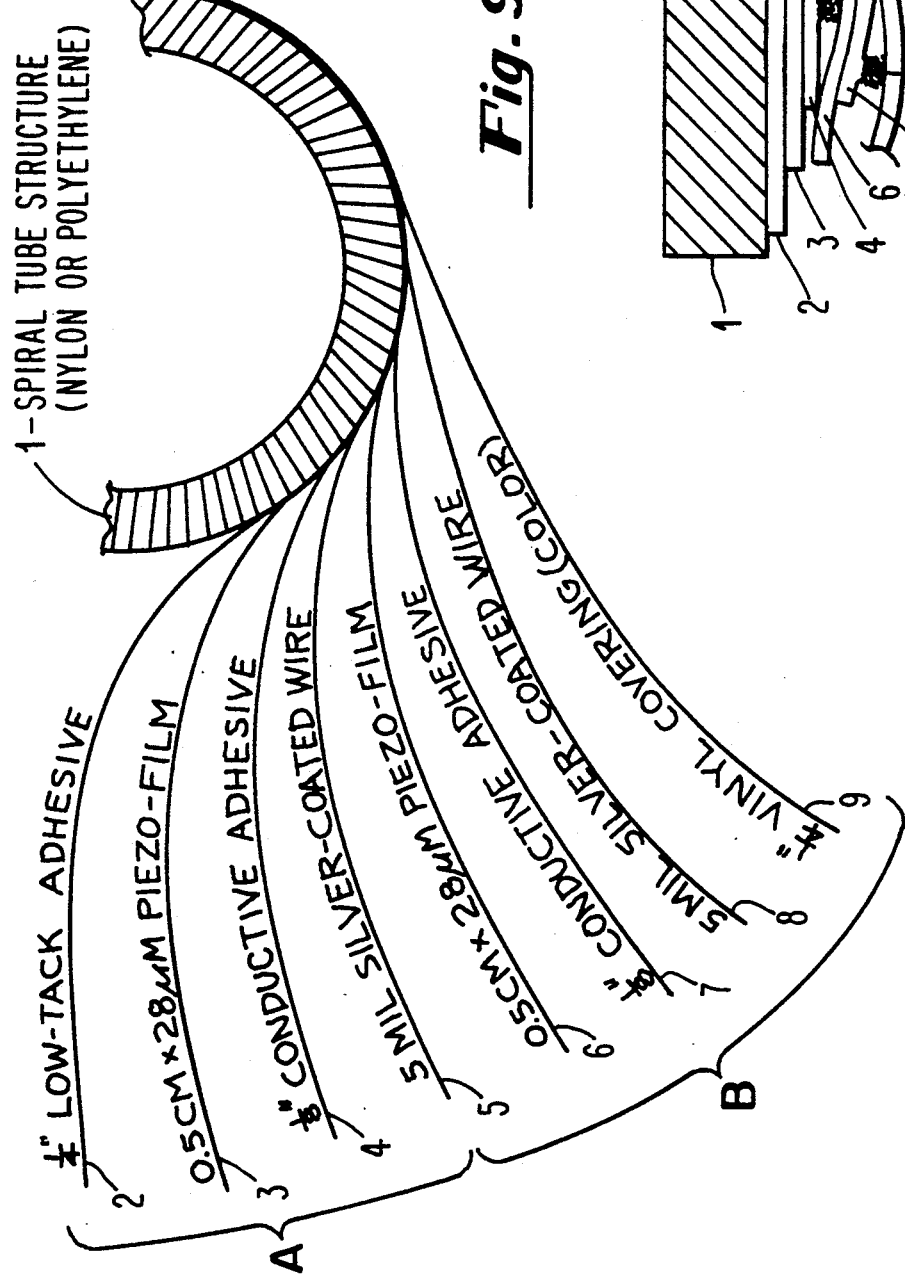
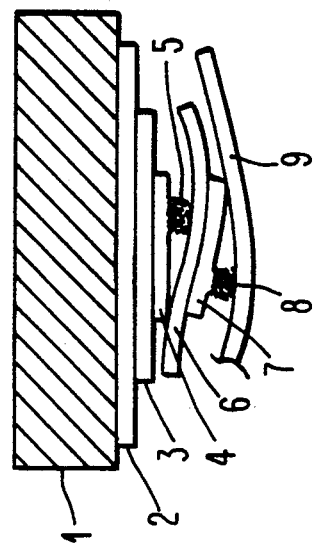

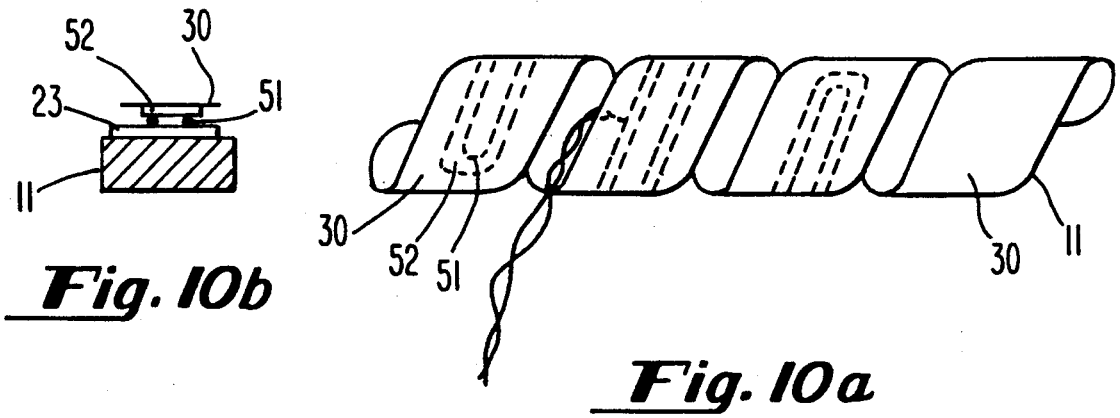
Fig. 10b
Fig. 10a
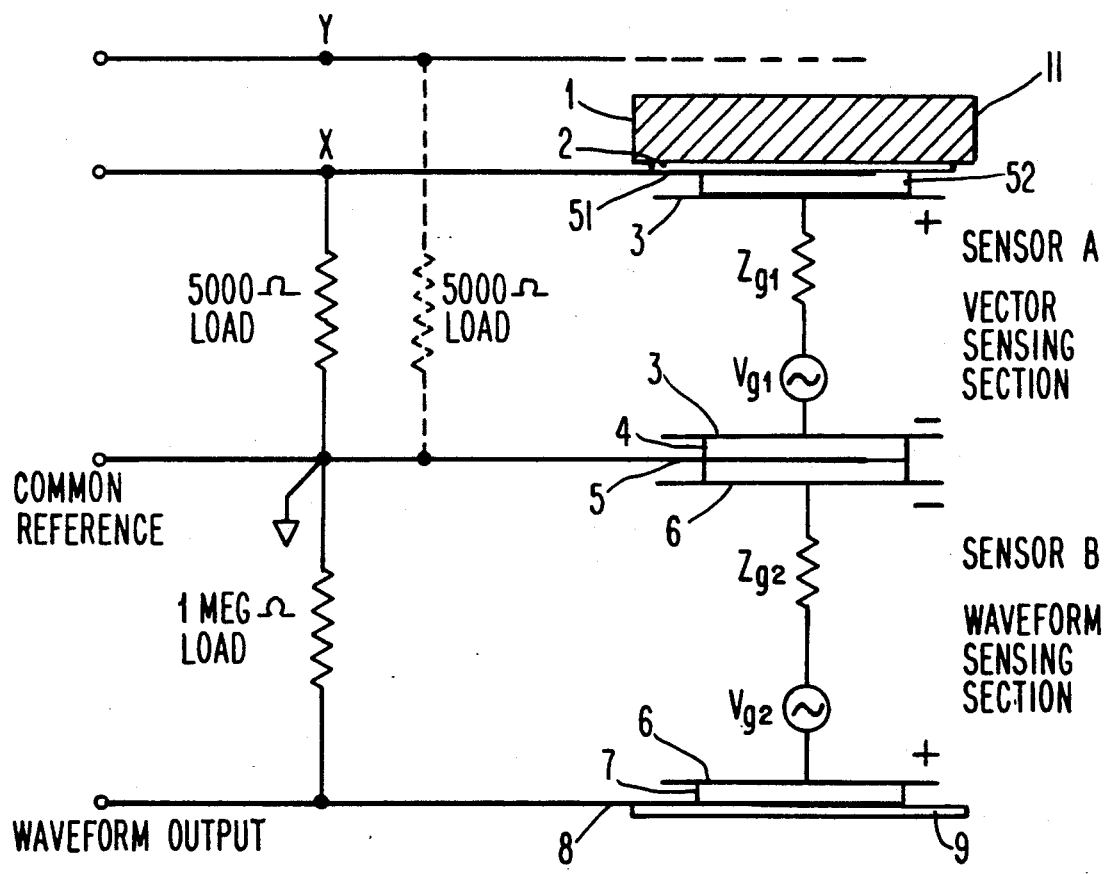
Fig. 11

SPIRAL SENSOR

FIELD OF THE INVENTION

The present invention relates generally to a device for generating electrical signals from the mechanical effort of a human patient. More particularly, the present invention relates to a spiral sensor which is particularly adapted to monitor mechanical heart response and respiratory or diaphragmatic effort around the chest, waist or like of a human patient.

BACKGROUND OF THE INVENTION

Present sensors for monitoring respiratory effort and other bodily functions generally consist of a flat strap or band that is placed around the torso of a patient and have only one sensing element. These body sensors have two common arrangements for sensing. A first arrangement involves the placement of a single sensing element at one location along a strap, normally at the attachment end. Typically, the sensing element is either a crystal or a ceramic, such as quartz or barium titanate respectively. The strap used is either an elastic-like waistband or girdle-like cloth belt. This arrangement relies upon the strap to transfer all respiratory activities to the point source sensor. The mechanical strains exerted on the strap by the respiratory expansion of the patient's thorax or abdomen are propagated through the strap to the point source sensor which then generates an electrical signal. One problem with this first arrangement is the inflexibility and cost of the sensing element. Crystals and ceramics are typically dense, brittle and stiff. These attributes impede the manufacture of sensors and render the fabrication of complex shapes impractical. The materials are also relatively expensive, resulting in high production costs. Another problem with this first arrangement arises from the reliance upon the strap to transfer torso movements to the point sensor and to provide adjustment means in attaching the sensor to patient. The material which comprises the strap generally dampens the mechanical force signal, thereby resulting in an electrical signal which may not fully reflect the actual respiratory and diaphragmatic efforts of the patient. This dampening effect also increases the likelihood of signal noise and artifacts.

The second common arrangement of body sensors employs a continuous flat strip of sensing material, typically a wire or film, running the length of the strap. The strap used in this arrangement is generally a stiff, belt-like device which, in conjunction with the flat strip of sensing material, maintains a continuous, singular surface contact with the patient. One problem with this arrangement is the prospect that patient position may occlude a large portion of the mechanical force signal, resulting in a weak electrical signal. Another problem is the relatively low signal-to-noise ratio which is the consequence of the inflexible belt-like device, i.e., stiffness in the belt increases the chance that extraneous forces will be exerted upon the sensing element, thereby resulting in relatively large signal artifacts. In applications where flat surface sensors are used, the piezo-film is laminated between two protective surfaces, protecting the thin metallization coating from being damaged or overstressed. However, when the piezo-film is wound on a curved surface, as is done in the structure of this invention, the outer metallization surface is placed under tension. When the thin outer metallization is stressed, the extremely thin film starts to develop invisible hairline fractures or cracks across the width of the piezo-film. Such hairline fractures initially cause an increase in conductive resistance, and eventually can lead to an electrical open or break. It is thus necessary to recognize this potential problem, and to provide an effective solution for it.

Another problem with a belt or strap-like sensor is the method used to attach the sensor and belt around the patient. If the sensor does not contain any elastic means, it is very difficult to provide good adjustment and compliance with the wide variation of body sizes and normal changes around the waist of the patient due to respiratory function. The Spiral-Cord of this invention is a unique structure where an elastic adjustment means is built into each spiral loop, not requiring a separate elastic strap or a separate attachment and adjustment structure.

SUMMARY OF THE INVENTION

The present invention overcomes the disadvantages and limitations of the prior art by providing a means for minimizing artifacts and interference in the recording of mechanical forces by the sensing element. A thin piezo-film is attached along an entire length of a spiral tube. The spiral tube is made by slitting polyethylene or nylon tubing which is wound about a mandrel having an axial outer diameter slightly greater than the axial inner diameter of the tubing. This winding procedure forces the tubing to expand, and also creating equal spaces between each 360° turn in the spiral. When the piezo film is attached to the outer surface of the spiral tube, the film is essentially segmented by the spiral loops to effect a plurality of sensing surfaces equally spaced around the patient and making independent contact with the body surface. In addition to winding the piezo film about a spiral cord, a separate conductor is attached substantially along the outer surface of the film, making electrical contact with the film using a conductive adhesive. This wire maintains electrical continuity for the entire linear length (approximately 280 cm) of the Spiral-Cord. Since complete surface area continuity is maintained, there is no degradation of the performance of the film.

There are a number of significant advantages of this invention over the prior art. First, the unique spiral sensing design herein employed creates a high quality output signal which can be connected directly to a recording or other like device. Approximately 100 sensing surfaces make operative contact with the patient's body contour when the spiral sensor is placed around the patient. Each sensing surface detects mechanical body forces and generates a corresponding electrical signal. The generated signals are then essentially summed to produce an output signal indicative of true respiratory effort with minimum artifacts.

Still another advantage of this invention over the prior art is the result of the inherent longitudinal flexibility of the plastic tube, which allows for adaptation about a variety of body portion sizes. This differs greatly from the prior art which generally employs stiff, and somewhat inflexible belts of a known length. Additionally, the piezo film expands and contracts with the spiral tube while maintaining good electrical conduction due to the separate wire conductor attached along the outer surface of the film. The wire conductor basically jumps any conductive breakage or discontinuities which may occur under extreme tensile stresses.

The primary object of this invention is to provide a body sensor which generates a clean and responsive output signal indicative of mechanical effort with minimal artifacts and signal interferences. The body sensor is adapted to different sized body portions, and provides effectively separate sensing elements which self-align to different body contours, and provide accurate dynamic sensing to changes in physiological functions.

Another object of this invention is to provide an improved method of constructing a spiral body sensor whereby signal quality and conductive integrity are maintained.

It is another object to provide a sensor adapted to surround a portion of a patient's body which can locate and measure a mechanical force vector originating within the body portion.

It is yet another object of this invention to provide a multi-layer spiral-cord apparatus with separate and independent sensing elements.

It is a still further object of this invention to provide a piezo-film sensor that can be electrically activated, converting it into a mechanical stimulator for delivering a mechanical stimulus along the length thereof. In a multi-layered embodiment of this invention, one layer can be used to generate a mechanical stimulus while a second layer is employed to sense body mechanical response to the stimulus.

BRIEF DESCRIPTION OF THE DRAWINGS

FIG. 9a is a schematic illustrating the component elements of a two-transducer, or two-layer sensor; FIG. 9b is a schematic cross-section of a two-layer sensor.

FIG. 10a and 10b are schematic representations of an electrical connection to one end of a piezo-film transducer.

FIG. 11 is a circuit representation of a two layer sensor.

DETAILED DESCRIPTION OF THE PREFERRED EMBODIMENTS

Figure 1A:
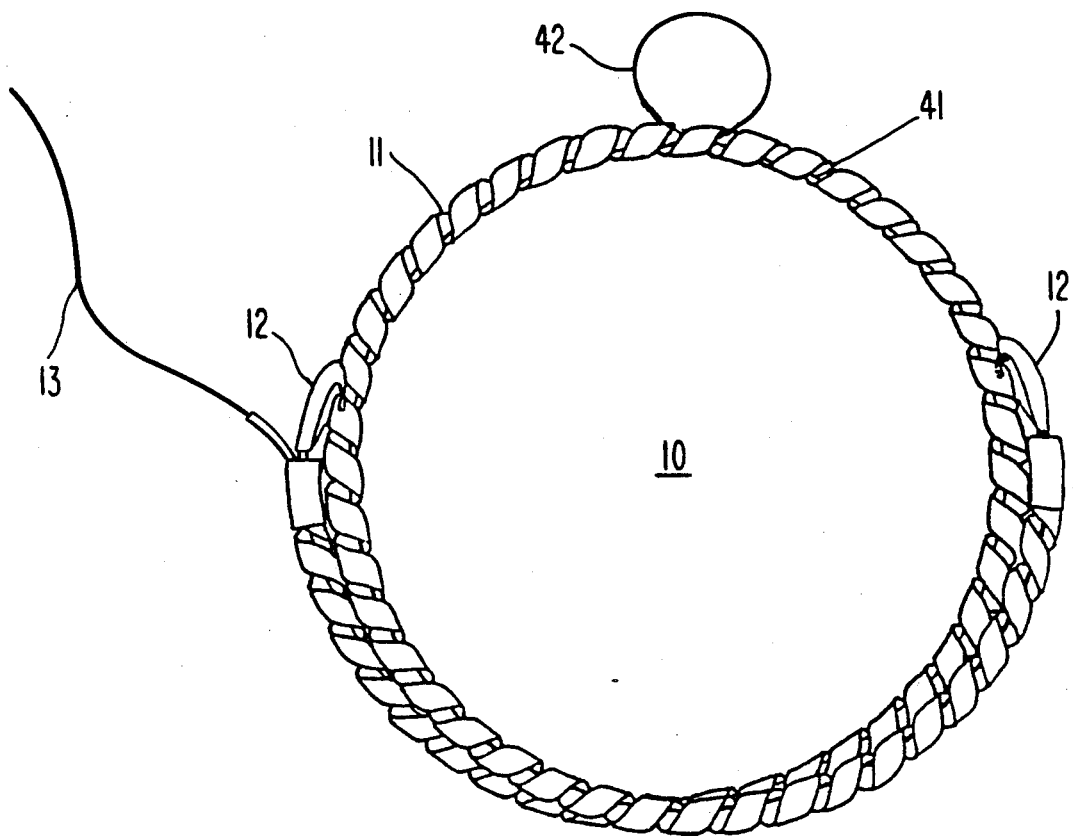
FIG. 1a is a perspective view of the device in accordance with the present invention.

The preferred embodiments of the present invention will now be described, referring to the drawings.

Referring to FIG. 1a, there is shown a sensor 10 according to the present invention. The sensor 10 detects mechanical forces originating in a patient's body and converts these mechanical forces into an electrical signal. The electrical signal is generated by using a transducer (see FIG. 3) comprising a piezo-electric film having an outer metallization surface and an inner metallization surface. Each metallization surface has a thickness of about 250 Angstroms; the piezo-electric film has a thickness of about 28 micrometers. For many applications, a typical length is about 280 cm, and the width is approximately 0.5 cm. The film is electrically polarized and when subjected to mechanical strain, e.g., expansion of a patient's thorax or abdomen during respiratory activity generates an electrical output signal. This polarization is directly proportional to the strain exerted. While it is understood that several different materials may exhibit piezoelectricity, the present invention employs a polyvinylidene fluoride (PVDF) film as the transducer element. PVDF is strong, lightweight, flexible and has the ability to resist contamination from chemical solvents. Additionally, PVDF is more sensitive than other transducer materials as a transformer of mechanical to electrical energy. PVDF piezo film has an impedance between opposing metallization surfaces in excess of 20 meg ohms and a lengthwise metallization impedance of each matalized surface is approximately 5000 ohms for a lineal length of 280 cm.

The transducer is attached to a spiral tube 11 of a predetermined length and width. The tube 11 is preferably comprised of slitted polyethylene or nylon tubing which has approximately 8 millimeters of tubing surface between each slit and an inner axial diameter of nearly 7 millimeters. The tubing is longitudinally expanded as it wound upon a mandrel so that it forms a spiral cord with predetermined spaces between each 360° turn in the spiral (see FIG. 2). This spiral, combined with the inherent flexibility of the slitted plastic tube, provides a longitudinal flexibility necessary for easy adaptation of the sensor around any body portion of the patient.

Two types of solid plastic or metal-type tubes can be used as the substrate for the Spiral-Cord. The primary property of the spiral material is that it is spring-like and returns to its original shape after being extended and released. For normal monitoring applications (respiration and heart pulse) the material shall respond without any hysteresis and maintain proper (linear) frequency response within the band width set for the given monitoring application. For a typical spiral-cord as shown in FIG. 1a, the band width 3 db points are 0.2 Hz and 50 Hz.

Figure 1B:
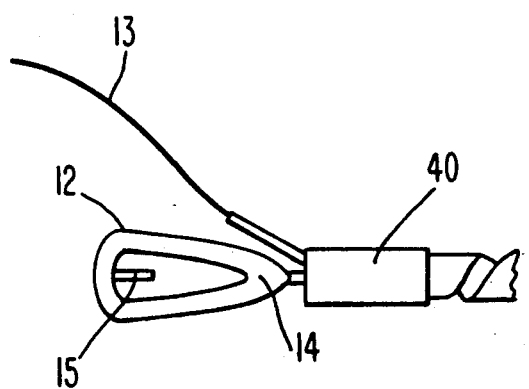
FIG. 1b illustrates an end hook on the device in accordance with the present invention.

Since piezo film needs no power supply to function, the sensor is put into operative position by simply connecting end hooks 12, which are attached to each end of the spiral tube 11, dto turns in the adjacent spiral illustrated in FIG. 1a. FIG. 1b illustrates one end hook 12 in more detail. End hook 12 includes a vinyl coating 14 and a locking pin 15. The locking pin 15 mechanically secures the end hook 12 to the spiral tube 11 when attached around a human patient (see FIG. 1a), while the vinyl coating 14 provides sufficient friction to prevent the end hook 12 from rotating about the spiral tube 11.

Figure 2:
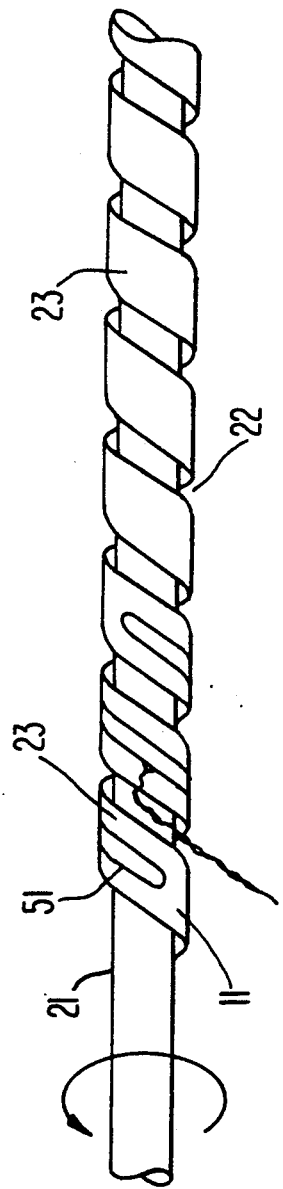
FIG. 2 illustrates the spiral sensor in the first stages of construction in accordance with the present invention.

Referring back to FIG. 1a, the electrical lead 13 is adapted to carry the electrical signal generated by the sensor 10 to a recording device (not shown), or other available display and/or storage device. The lead 13 can be a common copper wire cable. The lead 13 is soldered to each terminal end of the sensor comprised of a 5 mil wire loop 51 type of termination as shown in FIG. 2. Also lead wires in lead 13 are soldered directly to a 5 mil conductor wire 34 (see FIG. 3) which is attached to one side of the transducer and runs the entire length, as discussed below.

As shown in FIG. 2, the spiral tube 11 is prepared by winding it on a mandrel 21 having a diameter that is greater than the inner diameter of the spiral tube 11 so that, when fully wound, spaces 22 of approximately 3 millimeters each are created between adjacent tube surfaces, i.e., between each 360° turn in the spiral tube 11. Each 360 turn constitutes approximately 11 millimeters length of tubing, in an illustrative case.

A standard, two-sided adhesive strip 23 is applied along the length and within the center of the outer surface of the spiral tube 11. The adhesive strip 23 can be a carrier-type tape with acrylic adhesive on both sides of the tape; one side should have a high tack, permanent adhesive while the other side has a low tack adhesive. The high tack surface of the adhesive strip 23 is attached to the outer tube surface. The low tack surface of the adhesive strip 23 is left unapplied until a transducer is attached thereto (see FIG. 3). By attaching the transducer to the low tack surface of the adhesive strip 23, the flexibility and longitudinal movement of the transducer and spiral tube 11 are facilitated without compromising the stability of the thin metallized conductive coating of the transducer (not shown).

Figure 3:
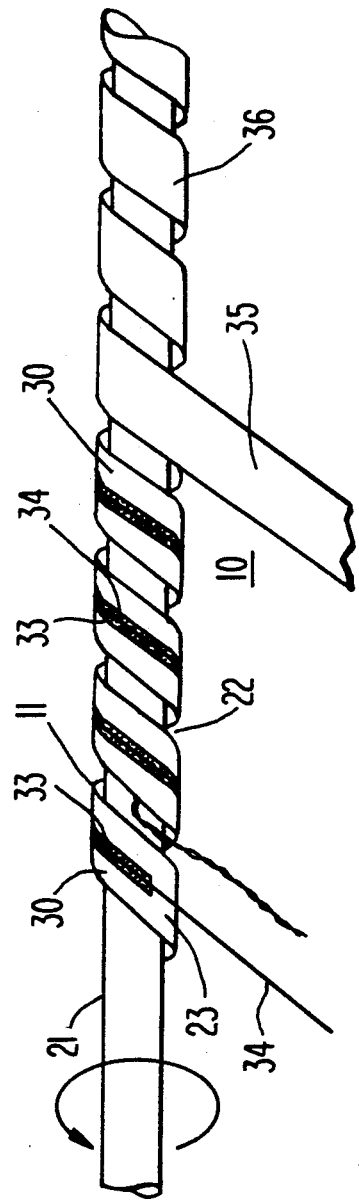
FIG. 3 illustrates the spiral sensor in the middle stages of construction in accordance with the present invention.

Referring to FIG. 3, there is shown a more detailed illustration of the sensor 10. A transducer 30 is attached to the low tack surface of the adhesive strip 23 and along the length and center of the spiral tube 11. By winding the transducer 30 about the spiral tube 11, the transducer 30 adopts the spiral cord shape which includes maintaining spaces 22 of approximately 3 millimeters wide between each 360° turn of the transducer 30. As a result of the spiralling technique employed to construct the sensor, when the spiral sensor 10 is placed about a body portion, a plurality of equally spaced sensing surfaces 36 come into operative contact with the patient. Since each sensing surface 36 is approximately half of the length of each 360° turn in the spiral (i.e., 6 millimeters) and the width of the surface 36 is approximately 8 millimeters, the total area that comes into contact with the body at each sensing surface 36 is approximately 50 square millimeters and is separated from an adjacent sensing surface by approximately 3 millimeters. The plurality of sensing surfaces 36 provides a high quality output signal with minimal signal interference and artifacts, by essentially generating individual electrical signals corresponding to individual mechanical forces detected by each sensing surface. These signals are summed to procedure a clean output signal.

Electrical connections are made at each end of the transducer film to provide output terminals. For connection to the inner film metallization surface, a 5 mil wire loop is used, which is attached to the film surface using a conductive adhesive (see FIGS. 2 and 10). For the outer surface, a similar loop can be used, or the output terminal can be connected to a 5 mil wire 34 (described below) which runs along the length of the outer surface (see FIG. 3).

As shown in FIG. 3, a two-sided, conductive adhesive strip 33 which can be acrylic with conductive particles such as silver-coated nickel is applied along the length of the outer surface of the transducer 30. Attached to the center and along the length of the conductive adhesive strip 33 is a wire conductor 34, suitably a 2-5 mil wire. The wire conductor 34 can be a common silver-coated copper wire, providing a low electrical resistance of less than 5 ohms. The wire conductor 34, together with the conductive adhesive strip 33, provides the means to maintain the conductive integrity of the transducer 30. The wire 34 is electrically connected to the transducer 30 through the conductive adhesive 33. As the transducer 30 is placed under various tensile stress conditions gaps may occur in the outer stressed metallization, i.e., a possible open circuit effect is created. The wire 34 provides a conductive bridge to transverse these potential gaps thereby preserving conductive integrity and high quality signal output.

A vinyl tape strip 35 with adhesive is applied along the outer surface of the sensor 10 to provide further protection from abrasions and fluid contaminations, as well as to provide some stability. After this tape strip 35 is applied, the mandrel 21 is removed from the center of the spiral tube 11.

Figure 4:
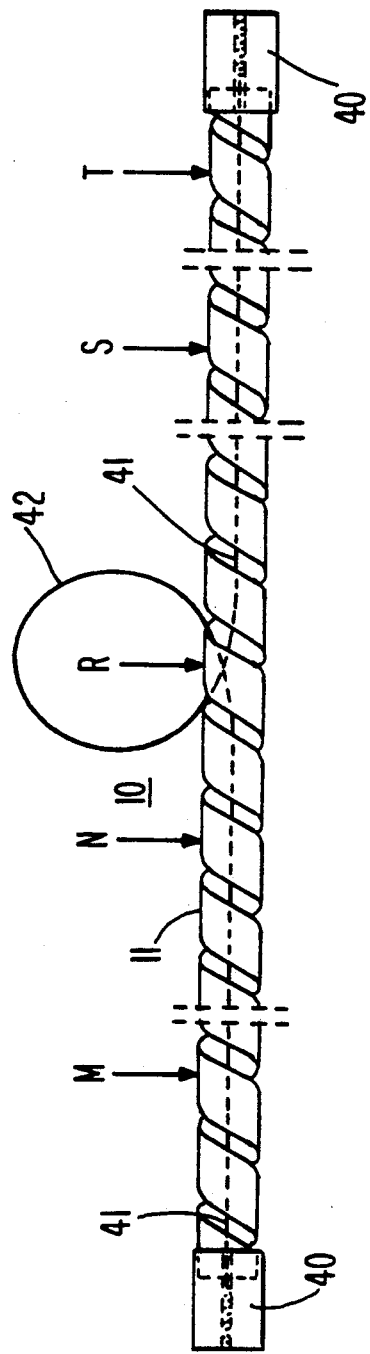
FIG. 4 illustrates the spiral sensor in the last stages of construction in accordance with the present invention.

Referring to FIG. 4, there are shown the mechanical and electrical termination assemblies of the sensor 10. Two stainless steel plugs 40, which are tapped to receive threaded bolts (not shown), are placed, one at each end of the spiral tube 11. One end of a coated wire 41 is then secured to one of the steel plugs 40, while the other end is fished along the axially center of the spiral tube 11 until it can be attached to the other stainless steel plug 40. The coated wire 41 performs several functions. First, the coated wire 41 effects a common-mode electrical ground. Second, it behaves as a visual tension loop 42, allowing the user to ensure proper usage. The coated wire 41 additionally behaves as a tether, preventing the spiral tube 11 and transducer 30 from becoming over-extended, thereby affecting sensing performance.

The stainless steel plugs 40 also permit the spiral sensor to be connected in series with another spiral sensor for adaptation around larger body portions or other objects which produce mechanical forces while maintaining the conductive integrity of both transducers.

In addition to the aforementioned applications of the spiral sensor, the sensor can be used to monitor cardiac effort and motor function of various muscles. Non-medical applications of the spiral sensors include robotics and traffic control monitoring. Due to the spiral sensor's inherent strength and flexibility, little or no modification is necessary to effect these different applications.

In many applications, it is important to be able to determine the direction from which the sensed signal has originated. Determining the force vector and its direction along the sensor, or "Spiral-Cord", requires a method to search for the vector and calculate its location. The piezo-film is a unique sensor because it does not require any external power or components to generate a signal when a mechanical force is applied. One can think of the piezo-film as composed of an infinite number of signal generators distributed throughout the film.

Figure 5:
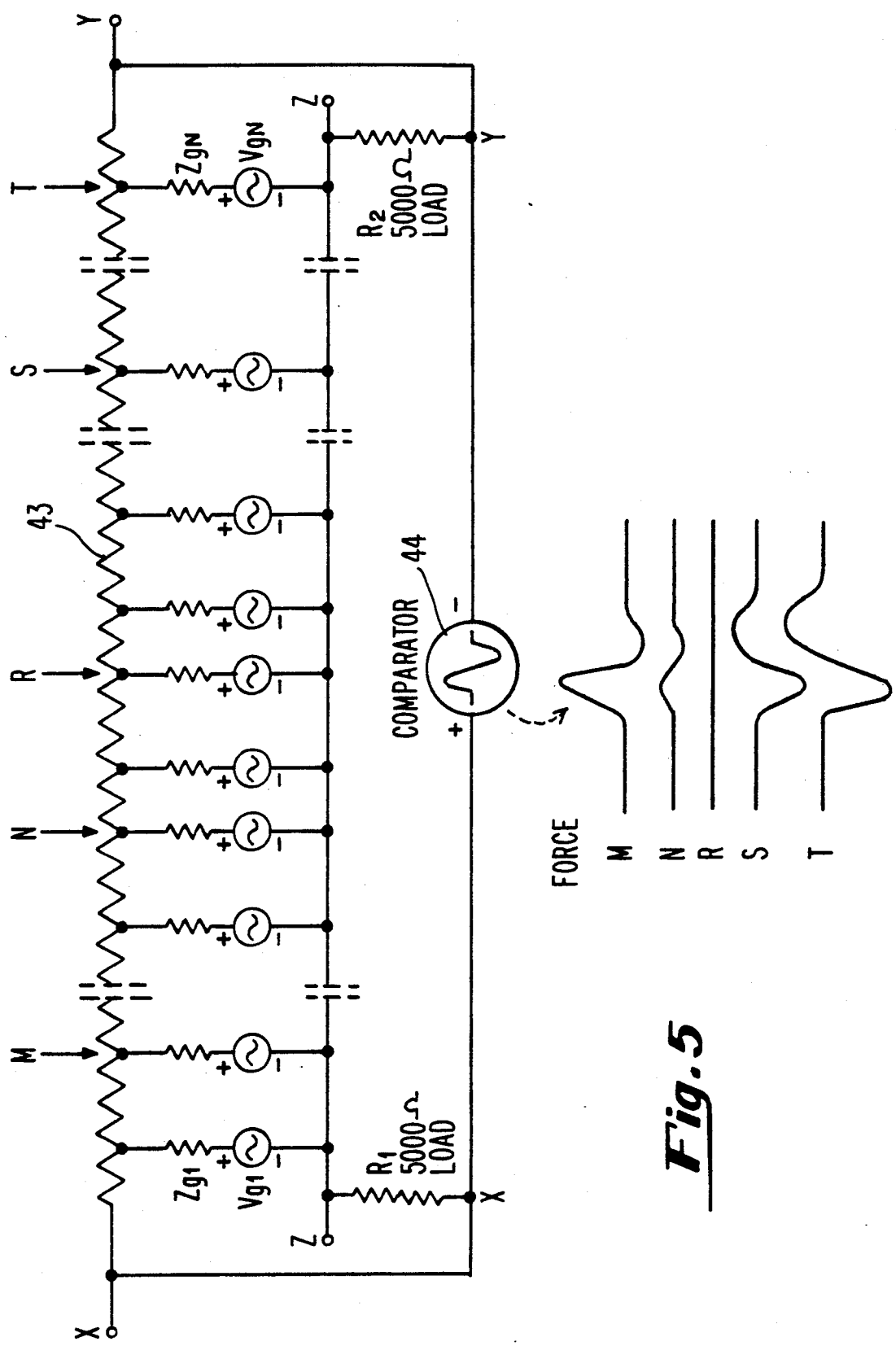
FIG. 5 is a schematic circuit representing a simplified electrical model of the cord sensor of this invention.

In FIG. 5, separate piezo signal generators are indicated for each spiral turn. For one embodiment of the Spiral-Cord there are at least 100 piezo signal generators corresponding to the 100 spirals or mini-sensors. The piezo generator generates a signal when there is a mechanical force applied to the spiral element(s) along the cord. In a simple example, Force M (upper left) is applied to the cord, resulting in a positive voltage across its respective piezo generator. The positive voltage also appears at terminals X and Y, referenced to Z. Besides monitoring the voltage level, it is important to know the location of Force M in reference to the cord length or vector position around the patient.

To locate Force M, there is another feature built into the construction of the Spiral-Cord. As stated earlier in the disclosure, the inner metallization (conductor surface) of the piezo-film is under compression and remains stable when the cord is extended or contracted in length. Because the piezo-film metallization is very thin (250 Angstroms), it acts like a metal resistor instead of a low impedance conductor. For example, the X-Y resistance is typically about 5,350 ohms, which is recorded in the relaxed state. When the cord is fully extended, the resistance slightly increases to 5,370 ohms, less than a 0.5% change in resistance value.

Figure 6:
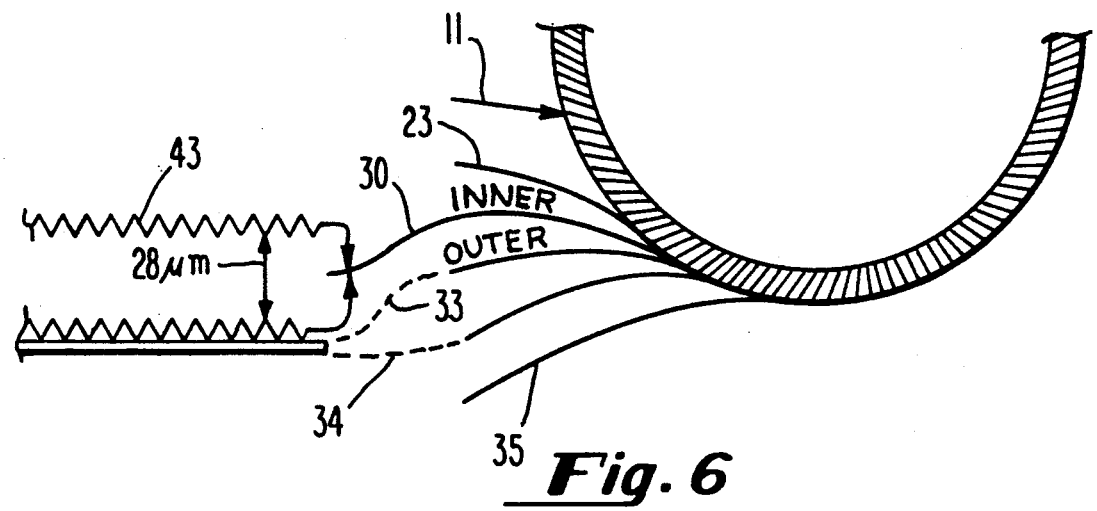
FIG. 6 is a schematic drawing which illustrates the elements of the sensor in spaced relation to each other.

Referring to FIGS. 5 and 6, the inner metal resistor 43 is located between X and Y terminals. Because the metal resistor 43 is very linear between X and Y, the linear resistance principle can be used to locate Force M. There are many ways one can arrive at the location of Force M, ranging from complex impedance calculations to simple empirical tests. Here, a simple comparator 44 is placed between the X and Y terminals. Also to simplify the comparator circuit and reduce the effects of any external loading, X and Y are illustrated as being terminated into a 5,000 ohm load (resistance close to the inner metal resistor value). Drawing 5 displays the comparator response for the applied Force M.

Because the Force M is applied very close to terminal X and far away from Y, the voltage signal at X will be large compared to the signal at Y. The reason for the difference in signal level is due to the voltage dividing along the inner metal resistor 43. Another way to look at the signal difference between X and Y is that the force voltage signal generated by the piezo generator M has a low resistance path to X but a higher resistance path to Y, therefore resulting in a differential voltage detected by the comparator 44.

Figure 7:
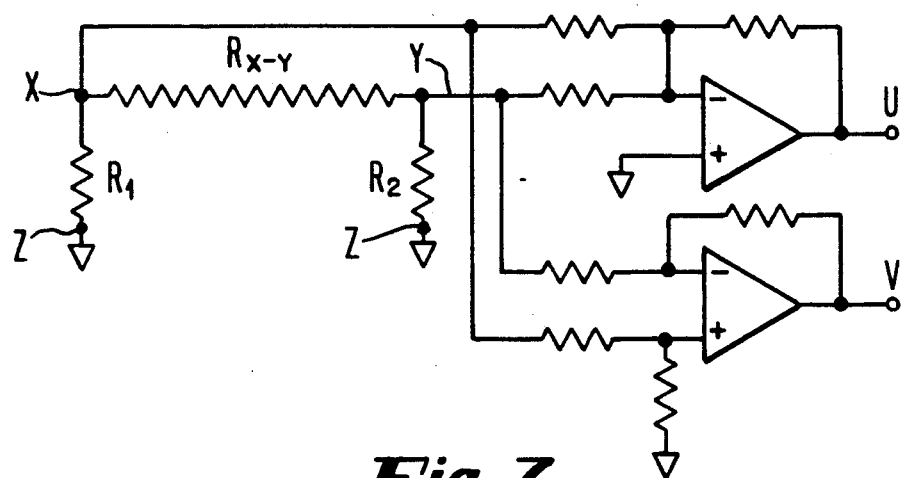
FIG. 7 is a circuit diagram showing a comparator circuit for providing signals from which force location can be determined for the sensor of FIG. 5.

Assume application of another force closer to the center of the cord at location N. The comparator indicates a small positive signal. As illustrated in FIG. 7, one way to precisely locate Force N is to compare the comparator signal V to the signal U which is the summed X and Y signals referenced to Z. The location of Force N is determined by calculating the signal ratio between U and V.

When a Force R is applied to the cord at its mid-point or center, the signal amplitude at X and Y will be identical and the comparator 44 will indicate no signal response. Take the case where a Force S is applied midway between the cord center and terminal Y. The signal at Y will be larger than at X resulting in a small negative signal at the comparator. Again the location of Force S will be achieved by comparing the ratio of peak voltage signals of U and V, independent of signal direction. Applying Force T very close to the Y terminal results in a very large negative signal V and very close in peak amplitude to signal U, indicating that Force T is in close proximity to terminal Y.

In practice, when the Spiral-Cord is applied around a patient, there is a complex series of forces distributed along the cord. There are force vectors from the heart, lungs and active muscles resulting in a summation of force signals at terminals X and Y. For example, if the user wants to locate the predominate force vector associated with the heart, an attempt is made to reduce to a minimum level the effects due to respiration and muscle activity. Even a clean mechanical heart signal is composed of many force vectors radiating from the heart to all of the 100 mini-sensor distributed around the patient. In this case it is desired to locate the predominate or largest summed force in reference to the circumference of the patient. This search for the predominate force vector requires more than a simple comparator to locate the vector.

Figure 8:
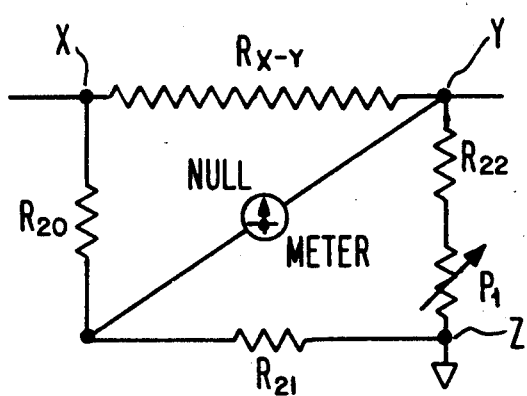
FIG. 8 is a null-bridge circuit used with the sensor of this invention for locating a predominate force vector sensed by the sensor of FIG. 5.

One method is to vary the load resistors R1 and R2 and monitor the voltage differential between terminals X and Y. From a measurement algorithm one can calculate and isolate the predominate or largest vector force. A second method is to use a null-bridge circuit shown in FIG. 8 and adjust the variable resistor P1 for a signal null. The predominate force vector will be at the resistance value of R22+P1 in relationship to the value of R(XY). Empirical testing is required to select the most sensitive and precise method to locate the predominate heart vector.

In many applications, it is desirable to have two electrically separated piezo-film sensors on the same spiral structure. One sensing element is terminated into a relatively low impedance and is used to locate the predominate force vector. The other sensor gives a good waveform representation of the mechanical signal with minimum distortion and signal loading.

Reference is made to FIGS. 9a, 9b, 10a and 10b, which illustrate a two-layer, or two transducer sensor. The fabrication methods described above remain basically the same except for the electrical connection method. Electrical connection is simply made at either end of the sensor by soldering directly to the 5 mil silver coated wire running the length of the cord, seen as elements 5 and 8 in FIGS. 9a and 9b. For electrical connection to the inner piezo-film metallization which does not contain a continuous 5 mil wire, a special 5 cm long 5 mil wire loop 51 is used. It is attached by a conductive adhesive 52 laid on the wire loop 51 (FIG. 10) and in contact with the piezo-film 30, at either end of the cord. A high-tack/low tack adhesive strip 23 is placed on the outer surface of the spiral element 11; the loop 51 is thus sandwiched between conductive adhesive 52 and adhesive strip 23. This attachment method is simple and the wire loop is constructed from the same 5 mil silver coated wire used in layers 5 and 8.

An electrical representation for the two piezo-film layers is given in FIG. 11. Sensor A, the first layer on the spiral structure, is electrically independent from the Sensor B, second layer. Because the two sensing elements share a common conductor (elements 4 and 5 in FIG. 9), this conductor is the common reference for the two sensors. As an example, in the construction of a cardiac force type Spiral-Cord sensor, the first layer (sensor A) becomes the Vector Sensor and the second layer (sensor B) becomes the Waveform Sensor. Each sensor is independently loaded and does not interfere with the performance of the other sensor. Because both sensors are monitoring the same mechanical forces, they are synchronized without any phase shifting or delays. This is not true when comparing an ECG waveform with a mechanical waveform.

The added sensor layer does create an increase in the sensor cord tension force which results in more force to maintain the same tension loop size. This increased tension force does not cause an attachment problem or discomfort to the patient. The only technical problem is a slight decrease in the upper frequency response due to the added mass. For cardiac force signals, this decrease in the upper frequency does not alter waveform shape o reduce the diagnostic quality of the signal.

Figure 12:
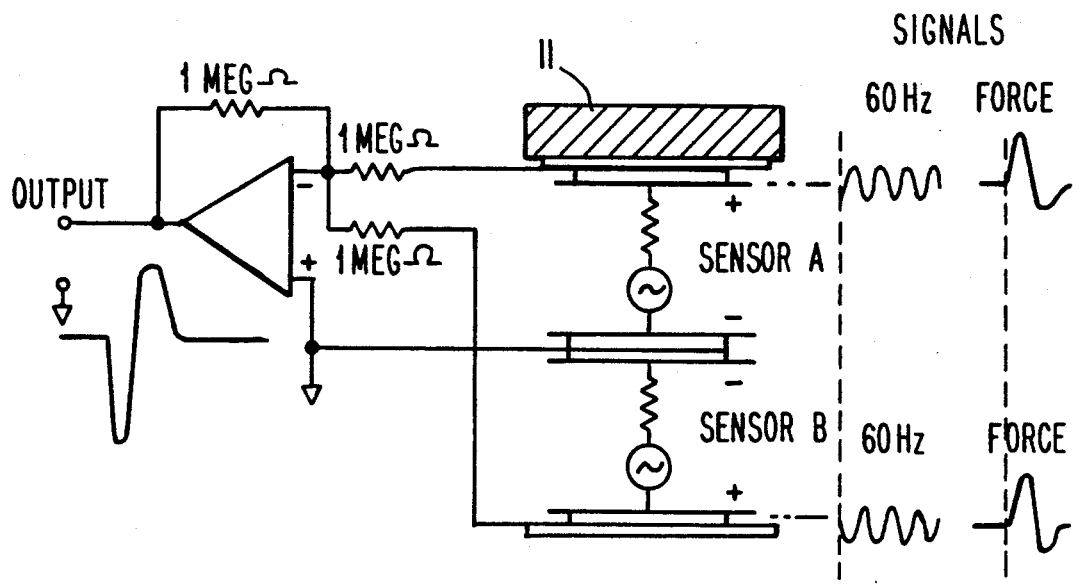
FIG. 12 illustrates a circuit for connecting two sensors of a dual sensor cord to provide noise rejection.

In a specific application of the dual sensor Spiral-Cord, the sensors are constructed to reject electrical signal interference while doubling the mechanical force signal. FIG. 12 shows the construction and interface of the two sensors with a summing amplifier. The main principle in achieving 60 Hz and RFI signal rejection is in the way the two piezo-film layers are wound on the spiral structure. The first layer (sensor A) is wound on the spiral with the positive (+) polarization metallization surface of the piezo-film becoming the inner surface and in direct contact with the spiral surface. The second layer (sensor B) is wound on the spiral with reverse polarity, the negative (−) surface in contact with sensor A; see FIG. 12 for polarity reference. Because the piezo-film (28 micrometers) and surface metallization (250 Angstroms) is very thin, 60 Hz and FRI can easily penetrate through the film and metallization surface. On the right-hand side of FIG. 12 is shown a 60 Hz and a mechanical force signal being sensed by sensors A and B. Notice the phase reversal of the 60 Hz signal and the in-phase direction for the force signal. On the left-hand side (FIG. 12) the two signals are summed in an amplifier, referenced to a common electrical contact between sensors A and B. The output from the amplifier shows the summation of the force signals with complete cancellation of the 60 Hz or any penetrating electrical interference.

In another embodiment of the sensor of this invention, three or more layers are wound on the spiral to achieve greater signal sensitivity. One application is to use the Spiral-Cord to monitor the low level signals (heart and body movement) emitted by a fetus within a mother. For low level signal detection it is critical to have a sensor with a high signal to noise ratio resulting in a high quality and reliable signal requiring minimum filtering and algorithm processing.

Figure 13:
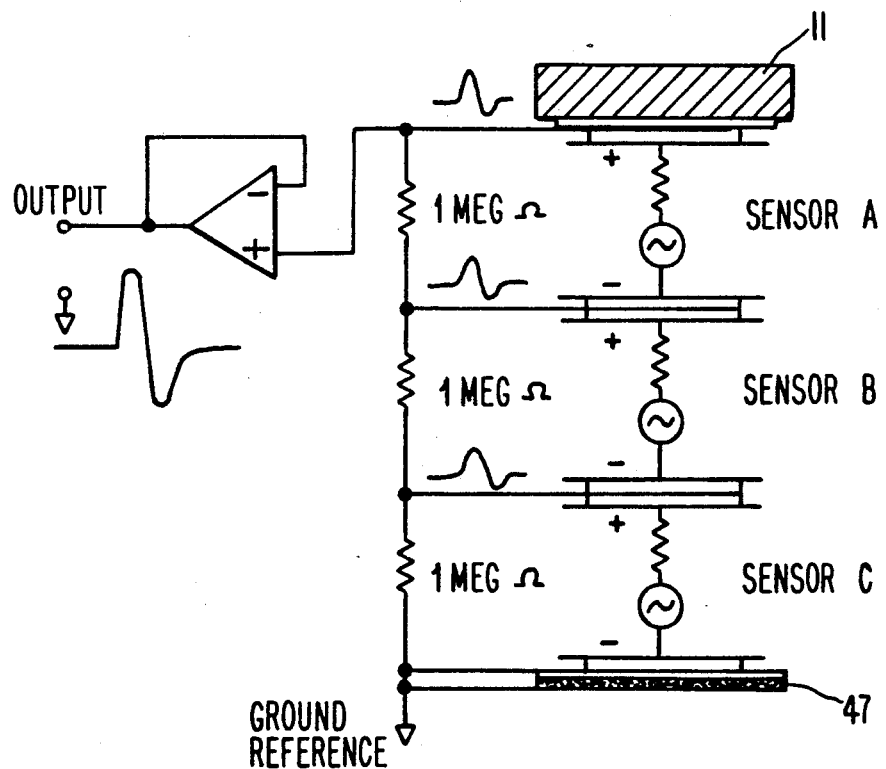
FIG. 13 illustrates a three-layer sensor and an output circuit.

FIG. 13 shows three piezo-film layers resulting in sensors A, B and C. Having the sensor (A, B and C) connected in series makes it possible to have any number of piezo-film layers to achieve the correct signal sensitivity. The limitation to the number of piezo-film layers on a Spiral-Cord depends on the maximum positioning tension of the cord and the require upper frequency response.

In constructing the multi-layer Spiral-Cord sensor of FIG. 13, the piezo-films are wound on the spiral using the same polarity direction for each layer. FIG. 13 shows the piezo-film polarity and the way the sensors A, B and C are connected in series using a 1 Meg load resistor across each sensor. One end of the series-connected 1 Meg ohm resistors is connected to non-inverting amplifier. The output from the amplifier shows the summation of the individual sensor elements A, B and C. To reduce RFI from penetrating the sensor elements, a flexible electrical conductor shield 47 is wound on the outer surface of the sensor and connected to ground reference.

Another of the unique properties of the piezo-film is that it not only senses a mechanical force, but it can generate a mechanical force. Instead of sensing a voltage signal at the terminals of the piezo-film, a variable voltage can be applied to the terminals causing the film to expand and contract.

Because the piezo-film is always under tension when it is wound on the spiral tube, any positive or negative voltage applied results in mechanical movement of the spiral structure. Depending on the force required to move the spiral structure, the piezo-film thickness will range from 9 to 110 micrometers, requiring an applied AC voltage from 50 to 500 volts.

Because of its compact size and ease of application, the sensor/stimulator can be very effective and efficient in applying a wide range of mechanical stimuli to body tissue. One example is to stimulate the head area to reduce muscle tension. Also, the spiral device can be used with a bio-feedback system where the patient can control his/her blood pressure or stress level with mechanical stimulation. Note that as claimed herein, the "sensor" device covers the use of the device as a stimulator, as well.

The mechanical stimulation embodiment can be taken a step further in using the multi-layer structure, where one layer is used to generate the mechanical signal and another layer is used to sense patient response to the mechanical stimulus. This stimulus and response feedback within a single structure provides excellent control in altering physiological events. A practical application is in the field of sleep medicine where one wants to induce delta (slow-wave) sleep while monitoring the patient's heart rate and muscular activity. The Spiral-Cord is placed around the patient's head and a low mechanical frequency (i.e., 7–8 Hz) is applied, helping to induce sleep. The low frequency stimulus signal is cancelled out from the sensing element so heart rate and body function can be monitored. One advantage for using mechanical stimulation instead of electrical stimulation is that it does not interfere with low level monitoring of ECG and EEG signals.

In a multi-layer sensor according to this invention, one layer can be mechanically activated and used to calibrate all the sensing layers. This can be very useful in applications where auto-calibration is required. Also the calibrator can be used as a modulator to enhance sensor performance or cancel out unwanted signals. Note that of the best calibrating signals found everywhere on the human body is the ever present heart pulse. The detected heart pulse can be used to calibrate the sensor at any location on the body, and the amplitude used to establish a calibration factor between the heart pulse and the monitored physiological signal.

While the present invention has been illustrated and described in connection with preferred embodiments, it is not to be limited to the particular structure shown. It is to be understood that various changes and modifications may be made within the purview of the appended claims without departing from the true scope and spirit of the invention in its broader aspects.

What is claimed is:

1. A sensor comprising:
    a) a spiral tube having a predetermined length and width;
    b) a transducer attached substantially along said spiral tube length and within said spiral tube width; and
    c) terminal means connected to said transducer for reading signals generated by said transducer.

2. The sensor as recited in claim 1, wherein said spiral tube has a predetermined longitudinal flexibility, said flexibility and said length combining to adapt said sensor for wrapping around body portions having a range of sizes.

3. The sensor as recited in claim 1, having spiral loop means for fixing said sensor around a body portion, whereby a plurality of segmented loop transducer surfaces are held in operative contact with said body portion.

4. The sensor as recited in claim 3, wherein said spiral loop means comprises:
   a) two terminal receptors connected to said spiral tube, one receptor connected to one end of said spiral tube, the second receptor connected to the opposing end of said spiral tube; and
   b) two end hooks attached to said terminal receptors.

5. The sensor as recited in claim 4, wherein said terminal receptors comprise cylindrical, threaded steel plugs.

6. The sensor as recited in claim 4, wherein said end hooks comprise:
   a) a vinyl or silicone rubber coating applied substantially about each surface of said end hooks; and
   b) a locking pin emanating from said vinyl or silicone rubber coating.

7. A sensor comprising:
   a) a spiral tube having a predetermined length and width;
   b) a transducer having an inner and outer surface, said inner surface attached substantially along said spiral tube length and within said spiral tube width;
   c) terminal means connected to said transducer for reading signals generated by said transducer; and
   d) conductive means attached along a substantial length of said outer surface of said transducer for maintaining conductive integrity along said transducer.

8. The sensor as recited in claim 7, wherein said spiral tube comprises a plastic or metal material of given flexibility.

9. The sensor as recited in claim 8, wherein said plastic material is polyethylene or nylon.

10. The sensor as recited in claim 7, wherein said transducer comprises a piezo film.

11. The sensor as recited in claim 10, wherein said piezo film has two opposing metallized surfaces, one outer metallized surface and one inner metallized surface.

12. The sensor as recited in claim 11, wherein said piezo film has an impedance between the opposing metallized surfaces in excess of 20 meg ohms.

13. The sensor as recited in claim 11, wherein said piezo film inner metallized surface has an end-to-end impedance of approximately 5000 ohms, and said conductive means has an impedance of less than 5 ohms.

14. The sensor as recited in claim 7, wherein said conductive means comprises:
   a) a conductive adhesive applied substantially along the length of the outer surface of said transducer; and
   b) a wire attached substantially along said conductive adhesive for the length of said transducer.

15. The sensor as recited in claim 14, wherein said wire comprises a silver-coated copper wire.

16. A multi-transducer sensor, comprising a spiral tube having an outer face and a predetermined length and width, a first transducer having an outer surface and attached substantially along said outer face of said spiral tube length, a second transducer attached substantially along said outer surface of said first transducer, and terminal means connected to each of said transducer for providing respective signals generated by each of said transducers.

17. A sensor as described in claim 16, wherein each of said transducers has a predetermined polarity.

18. The sensor as described in claim 16, comprising a common electrical reference between said first and second transducers.

19. A method for determining the force vector of a force generated within a portion of a human body, comprising
   a) providing a sensor having a spiral tube with an outer surface, a transducer attached substantially along said outer surface of said spiral tube and terminal means connected to said transducer for outputting transducer signals,
   b) connecting said spiral tube sensor around said body portion,
   c) connecting said transducer terminal means to processing circuitry and processing said signals to determine at least approximately where along the length of said sensor the force vector is located.

20. A stimulator comprising:
   a) a spiral tube having a predetermined length and width;
   b) a transducer attached substantially along said spiral tube length and substantially within said spiral tube width; and
   c) energizing means connected to said transducer for delivering stimulus signals thereto, whereby said transducer provides a mechanical response.

21. The method as described in claim 19, wherein said transducer has opposite ends, and comprising connecting said terminal means to said transducer opposite ends, and comparing signals generated at said opposite ends.

22. A combination stimulator and sensor, comprising:
   (a) a spiral tube having a predetermined length;
   (b) a first transducer attached along at least a first portion of said spiral tube length;
   (c) a second transducer attached along at least a second portion of said spiral tube length;
   (d) energizing means connected to said first transducer for delivering stimulus signals thereto, whereby said first transducer provides a mechanical response; and
   (e) sensor means connected to said second transducer for providing signals generated by said second transducer.

* * * * *

UNITED STATES PATENT AND TRADEMARK OFFICE
CERTIFICATE OF CORRECTION

PATENT NO. : 5,207,230

DATED : May 4, 1993

INVENTOR(S) : David L. Bowers

It is certified that error appears in the above-identified patent and that said Letters Patent is hereby corrected as shown below:

In column 9, line 2, after "shape" "o" should be --or--

Signed and Sealed this

Twenty-fifth Day of January, 1994

Attest:

BRUCE LEHMAN

Attesting Officer

Commissioner of Patents and Trademarks